(12) United States Patent
Kilger et al.

(10) Patent No.: US 6,605,428 B2
(45) Date of Patent: *Aug. 12, 2003

(54) METHOD FOR THE DIRECT, EXPONENTIAL AMPLIFICATION AND SEQUENCING OF DNA MOLECULES AND ITS APPLICATION

(75) Inventors: Christian Kilger, Heidelberg (DE); Svante Paabo, Leipzig (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

This patent is subject to a terminal disclaimer.

(21) Appl. No.: 09/339,104

(22) Filed: Jun. 24, 1999

(65) Prior Publication Data

US 2003/0134276 A1 Jul. 17, 2003

Related U.S. Application Data

(63) Continuation-in-part of application No. 08/991,347, filed on Dec. 16, 1997, now Pat. No. 6,107,032.

(30) Foreign Application Priority Data

Dec. 20, 1996 (DE) .......................................... 196 53 439

(51) Int. Cl.$^7$ .......................... C12Q 1/68; C12D 19/34; C07H 21/02; C07H 21/04; C07H 19/00

(52) U.S. Cl. .......................... 435/6; 435/91.1; 435/91.2; 435/91.5; 435/183; 435/193; 536/22.1; 536/23.1; 536/24.3; 536/24.31; 536/24.32; 536/24.33; 530/350

(58) Field of Search .......................... 435/6, 89, 91.1, 435/91.2, 91.21, 91.31, 91.32, 91.33, 91.4, 91.41, 91.42, 91.5, 91.51, 183, 193; 326/22.1, 23.1, 23.2, 23.4, 23.5, 23.72, 24.3, 24.31, 24.32, 24.33, 24.5, 25.3, 25.32; 530/350

(56) References Cited

U.S. PATENT DOCUMENTS

| | | | | |
|---|---|---|---|---|
| 4,683,202 A | * | 7/1987 | Mullis | 435/91 |
| 4,962,020 A | | 10/1990 | Tabor et al. | |
| 5,075,216 A | | 12/1991 | Innis et al. | |
| 5,338,671 A | * | 8/1994 | Scalice et al. | 435/91.2 |
| 5,409,811 A | | 4/1995 | Tabor et al. | |
| 5,427,911 A | | 6/1995 | Ruano | |
| 5,512,462 A | | 4/1996 | Cheng | |
| 5,556,772 A | | 9/1996 | Sorge et al. | |
| 5,587,287 A | | 12/1996 | Scalice et al. | |
| 5,614,365 A | * | 3/1997 | Tabor et al. | 435/6 |
| 5,677,152 A | * | 10/1997 | Birch et al. | 435/91.2 |
| 5,693,517 A | * | 12/1997 | Gelfand et al. | 435/193 |
| 5,789,168 A | | 8/1998 | Leushner et al. | |
| 5,830,657 A | * | 11/1998 | Leushner et al. | 435/6 |
| 5,994,056 A | * | 11/1999 | Higuchi et al. | 435/6 |
| 6,107,032 A | * | 8/2000 | Kilger et al. | 435/6 |

FOREIGN PATENT DOCUMENTS

| | | | |
|---|---|---|---|
| EP | 0 727 496 | 8/1996 | |
| EP | 0 771 870 | 5/1997 | ............ C12N/9/99 |
| WO | 94/05797 | 3/1994 | |

OTHER PUBLICATIONS

Amersham User Manual, US 78500, pp. 1–41, 1995.

Amersham Catalog, p. 368, 1996.

Chemical Abstracts, vol. 125, No. 25, p. 393, 125:319052, 1996.

Deng et al., "Simultaneous Amplification and Sequencing of Genomic DNA (SAS) . . . ", Journal of Microbilogical Methods, vol. 17, pp. 103–113, 1993.

Hwang et al., "Direct Automated Sequencing of Single Lambda–Phage Plaques by Exponential Amplication Sequencing", Analytical Biochemistry, vol. 231, No. 2, pp. 460–463, Nov. 1995.

International Publication No. WO 93/02212, published Feb. 4, 1993.

International Publication No. WO 94/26766, published Nov. 24, 1994.

International Publication No. WO 96/10640, published Apr. 11, 1996.

International Publication No. WO 96/41014, published Dec. 19, 1996.

International Publication No. WO 97/23650, published Jul. 3, 1997.

International Publication No. WO 97/40939, published Nov. 6, 1997.

International Publication No. WO 97/41257, published Nov. 6, 1997.

(List continued on next page.)

*Primary Examiner*—Jeffrey Siew
(74) *Attorney, Agent, or Firm*—Arent Fox Kintner Plotkin & Kahn, PLLC

(57) ABSTRACT

A method is described for the direct, exponential amplification and sequencing ("DEXAS") of a DNA molecule from a complex mixture of nucleic acids, wherein truncated DNA molecules as well as DNA molecules of full length are synthesized simultaneously and exponentially between two positions on the said DNA molecule, which initially contains a DNA molecule in a thermocycling reaction, a first primer, a second primer, a reaction buffer, a thermostable DNA polymerase, a thermostable pyrophosphatase (optionally), deoxynucleotides or derivatives thereof and a dideoxynucleotide or derivatives thereof. In a preferred embodiment of the method of the invention, direct sequencing of RNA can be performed using one polymerase having a Tabor-Richardson mutation, or a functional derivative thereof, and reverse transcriptase activity. In a more preferred embodiment of the method of the invention, direct sequencing of RNA can be performed in one step, in one vessel.

87 Claims, 8 Drawing Sheets

OTHER PUBLICATIONS

Figure 1:
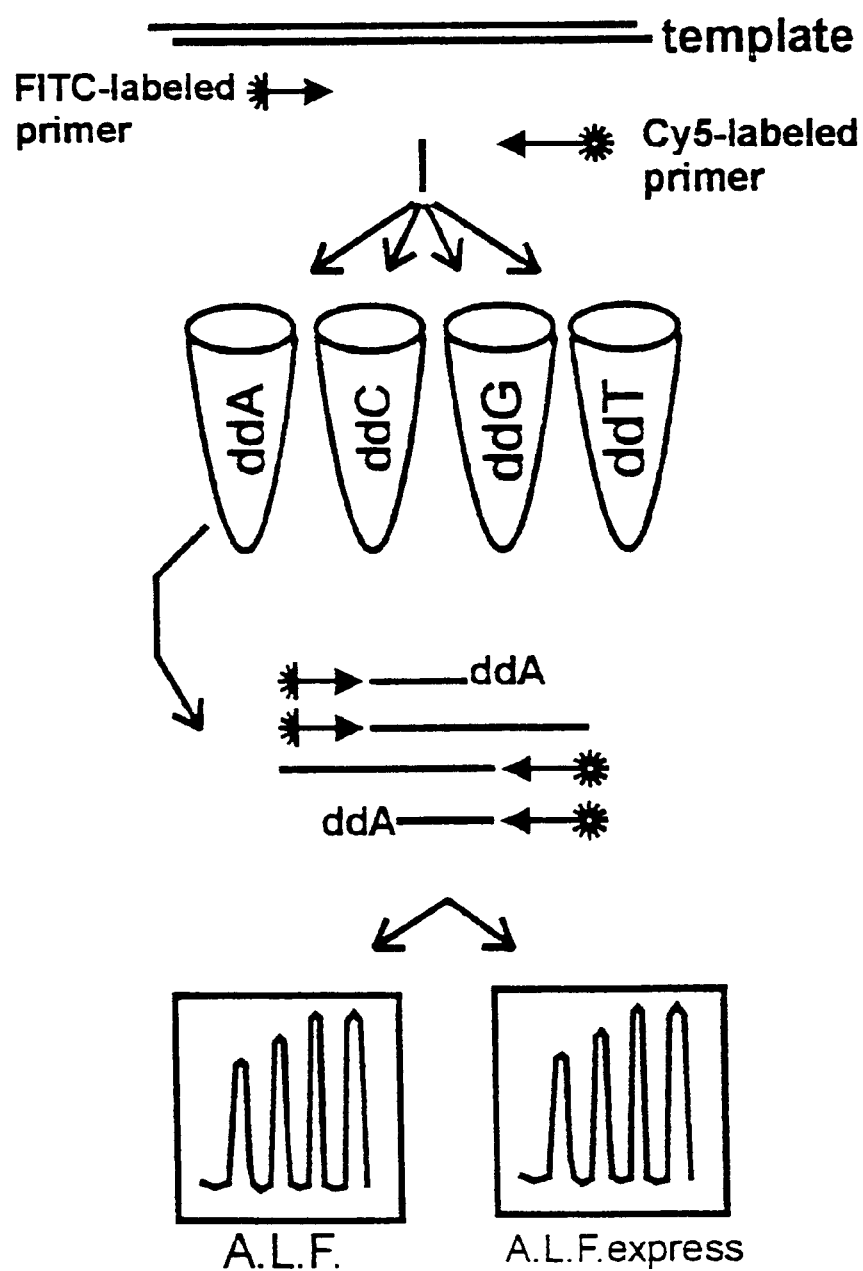

International Publication No. WO 97/41258, published Nov. 6, 1997.

International Publication No. WO 97/41259, published Nov. 6, 1997.

International Publication No. WO 97/42348, published Nov. 13, 1997.

Kilger et al., "Direct Exponential Amplification and Sequencing (DEXAS) of Genomic DNA", Biol. Chem., vol. 378, pp. 99–105, Feb. 1997.

Kilger et al., "Direct DNA Sequence Determination from Total Genomic DNA", Nucleic Acids Acids Research, vol. 25, No. 10, pp. 2032–2034, May 1997.

Rao, "Direct Sequencing of Polymerase Chain Reaction–Amplified DNA", Analytical Biochemistry, vol. 216, pp. 1–14, 1994.

Sarkar et al., "Semi Exponential Cycle Sequencing", Nucleic Acids Research, vol. 23, No. 7, pp 1269–1270, 1995.

Tabor et al, Proc. Natl Acad. Sci, U.S.A., "A Single Residue in DNA Polymerases of the *Escherichia Coli* DNA Polymerase 1 Family Is Critical for Distinguishing Between Deoxy–And Dideoxyribonucleotides", vol. 92, pp. 6339–6343, Jul. 1995.

* cited by examiner

Fig. 6A

```
ambiguities
Cy5         CNNCGAGTCG ACGGTATCGA TAACTTGATA TCGAATTCCT GCAGCCGGKK GGATCCGCCC    60
FITC ambiguities
Cy5         TACACCAGTC TTGTAAACCG GAAACAGAAA CTTTCTCCCC AGGGCAACTC AGAAAGAAAG   120
FITC ambiguities
Cy5         TACTCAACTT CACCACCAAC ATCCAAAACT GGCATTCTAA TTTAAACTAC TTTCTGCATT   180
FITC ambiguities                                                       YY K
Cy5         CTATGGGGGT GCAAGCTTTA AGTGCAACTT AAGTACTAAT TTATTATCA GACCCTTATG    240
FITC                                                  CTT AAGTACTAAT TTATTATCA GACCCTTATG     33 ambiguities                            T
Cy5         TAATTTGTGC ATTACTGCTA GCCAACATGA ATGTTATATA GTACTCATAA ATGCYTAACT   300
FITC        TAATTTGTGC ATTACTGCTA GCCAACATGA ATGTTATATA GTACTCATAA ATGYTTKACT    93 ambiguities                                             R
Cy5         GTACATAGCA CATATTTTWA CATACATACT ACATATTCTC AAGA-ACATG CTTACAAGCA   360
FITC        GTACATAGCA CATATTTTTA CATACATACT ACATATTCTC AAGARACATG CTTACAAGCA   153
                                                          R ambiguities
Cy5         AGAACCCCAA TGAACCAACC AACTGTAGAA CATAACATCA ACTTCAAAGA CCAAGCACAT   420
FITC        AGAACCCCAA TGAACCAACC AACTGTAGAA CATAACATCA ACTTCAAAGA CCAAGCACAT   213
                   M ambiguities
Cy5         CCCCMAGAAT ATCAACTAAC TTAACTTTTT ATTCATCATA CATAGCACAT TAAACGGTTC   480
```

```
FITC         CCCCCAGAAT ATCAACTAAC TTAACTTTTT ATTCATCATA CATRGCACAT TAAACGGTTC    273
ambiguities
Cy5          ATCGGACATA GCACATTTCA GTCAAACAAA TTCCTATCAC CACGGATACC CCCCTCAGTT    540
FITC         ATCGGACATA GCACATTTCA GTCAAACAAA TTCCTATCAC CACGGATACC CCCCTCAGTT    333
ambiguities                KK
Cy5          AGGTGTCCCT TATTCACCAT CCTCCGTGAA ATCAATATCC CGCACAAGAG TGCTACTCTC    600
FITC         AGGTGTKKCT TATTCACCAT CCTCCGTGAA ATCAATATCC CGCACAAGAG TGCTACTCTC    393
ambiguities
Cy5          CTCGCTCCGG GGGGCTAGAG CGGCCGCCAC CGCGGTGGAG CTCCMGCTTT TGTNCCCTTT    660
FITC         CTCGCTCCGG GGGG                                                      407
ambiguities
Cy5          ATGAGGCTC                                                            668
```

Fig. 6B

SEQUENCE LISTING

<160> NUMBER OF SEQ ID NOS: 10

<210> SEQ ID NO 1
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 1
gattctaatt taaactattc tctgttc                                27

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Primer -continued

<400> SEQUENCE: 2
ttatgaccct gaagtaggaa ccagatg                                               27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 3
ggaggcactt gccaccctgc acactgg                                               27

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 4
ctcctccacc gcttcttgtt ctgcttg                                               27

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
ggctggtcct gccgctgctt gtcat                                                 25

<210> SEQ ID NO 6
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 6
ctgctcccca gtggatcggg tgtaaac                                               27

<210> SEQ ID NO 7
<211> LENGTH: 326
<212> TYPE: DNA
<213> ORGANISM: Homo sapiens

<400> SEQUENCE: 7
ctsttaatst agtcgcttct cctccagcta cctggacctg gcgcttgggc tccagaaagg           60
accaagkgtg gttgggagta gatggagcct ggtttttttmw atgggacatg ggacaggtag         120
gacctgattt ccttactgcc tcttgcttct cttttcctat cctgagtagt ggtaatctac         180
tgggacggaa cagctttgag gtgcgtgtkt gtgcgtgtkt gtccctgtcc tgggagagac         240
cggcgcacag aggaagagaa tctccgcaag aaagggagc ctcaccacga gctgccccca         300
gggagcacta agcgaggtaa gcaagc                                              326

<210> SEQ ID NO 8
<211> LENGTH: 362
<212> TYPE: DNA
<213> ORGANISM: Homo sapiens

```
<400> SEQUENCE: 8
gmgtttggca atagtgcttt tggaagaaga ctaagaggtw ktttctgaac ttctccccga      60
caaaggcata gatgatgggg ttgatgcaga tggggttcat gcagcagtgc gtcatcccaa     120
gagtctctgt tyacctgcat agcttggtcc aacctgttag agctactgca attatttat     180 tcaggccaaa gaattcctgg aaggtgttca ggagaaggac aatgttgtag ggagcccaga    240
agagaaaata aacaatcatg atggtagata agcctcamag ccctgtgcct cttcttctca    300
tttcgacacc gaagcagagt ttttaggatt cccgagtagc agatgaccat gacaagcagc    360
gg                                                                  362

<210> SEQ ID NO 9
<211> LENGTH: 668
<212> TYPE: DNA
<213> ORGANISM: Homo sapiens
<220> FEATURE:
<221> NAME/KEY: modified_base
<222> LOCATION: (2)..(3)
<223> OTHER INFORMATION: a, t, c, g, other or unknown
<220> FEATURE:
<221> NAME/KEY: modified_base
<222> LOCATION: (653)
<223> OTHER INFORMATION: a,, t, c, g, other or unknown

<400> SEQUENCE: 9
cnncgagtcg acggtatcga taacttgata tcgaattcct gcagccggkk ggatccgccc      60
tacaccagtc ttgtaaaccg gaaacagaaa ctttctcccc agggcaactc agaaagaaag    120
tactcaactt caccaccaac atccaaaact ggcattctaa tttaaactac tttctgcatt    180 ctatggggt gcaagcttta agtgcaactt aagtactaat ttatttatca gacccttatg    240
taatttgtgc attactgcta gccaacatga atgttatata gtactcataa atgcytaact    300
gtacatagca catattttwa catacatact acatattctc aagaacatgc ttacaagcaa    360
gaaccccaat gaaccaacca actgtagaac ataacatcaa cttcaaagac caagcacatc    420
cccmagaata tcaactaact taacttttta ttcatcatac atagcacatt aaacggttca    480
tcggacatag cacatttcag tcaaacaaat tcctatcacc acggataccc ccctcagtta    540
ggtgtccctt attcaccatc ctccgtgaaa tcaatatccc gcacaagagt gctactctcc    600
tcgctccggg gggctagagc ggccgccacc gcggtggagc tccmgctttt gtnccctta    660 tgaggctc                                                            668

<210> SEQ ID NO 10
<211> LENGTH: 407
<212> TYPE: DNA
<213> ORGANISM: Homo sapiens

<400> SEQUENCE: 10
cttaagtact aatttatttta tcagacccctt atgtaatttg tgcattactg ctagccaaca     60
tgaatgttat atagtactca taaatgyttk actgtacata gcacatattt ttacatacat    120
actacatatt ctcaagarac atgcttacaa gcaagaaccc caatgaacca accaactgta    180
gaacataaca tcaacttcaa agaccaagca catcccccag aatatcaact aacttaactt    240
tttattcatc atacatrgca cattaaacgg ttcatcggac atagcacatt tcagtcaaac    300
aaattcctat caccacggat accccctca gttaggtgtk kcttattcac catcctccgt    360
gaaatcaata tcccgcacaa gagtgctact ctcctcgctc cggggggg              407
```

METHOD FOR THE DIRECT, EXPONENTIAL AMPLIFICATION AND SEQUENCING OF DNA MOLECULES AND ITS APPLICATION

This is a continuation-in-part application of U.S. patent application No. 08/991,347, filed on Dec. 16, 1997, the disclosure of which is herein incorporated by reference.

The present invention relates to a method for the direct, exponential amplification and sequencing of DNA molecules as well as the use of the method. The direct, exponential amplification and sequencing of DNA molecules is referred to as "DEXAS" in the following.

DESCRIPTION OF THE RELATED ART

DNA sequence determination as developed by Sanger et al. ((1977) *Proc. Natl. Acad. Sci. USA* 74, 5463–5467) is usually carried out with a T7 DNA polymerase (Tabor S. and Richardson, C. C. (1989) *Proc. Natl. Acad. Sci. USA* 86, 4076–4080). This method requires relatively large amounts of a purified, single-stranded DNA template. Recently cycle sequencing has been developed (Murray, V. (1989) *Nucleic Acids Res.* 17, 8889). This method does not require a single-stranded template and allows the sequence reaction to be initiated with relatively small amounts of template. However, the template DNA has to be purified to almost complete homogeneity and is usually prepared by means of cloning in plasmids (Bolivar, F. et al., (1977) *Gene* 2, 95–113) and subsequent plasmid purification (Birnboim, H. C. and Doly, J. (1979) *Nucleic Acids Res.* 7, 1513–1523) or by means of PCR amplification (Mullis, K. B. and Faloona, F. A. (1987) *Methods Enzymol.* 155, 335–350). Only one primer is used in both of the methods described above.

In one embodiment of the cycle sequencing which is referred to as "coupled amplification and sequencing" or "CAS" Ruano and Kidd ((1991) *Proc. Natl. Acad. Sci. USA* 88, 2815–2819; U.S. Pat. No. 5,427,911) have shown that one can use a two-step protocol to generate sequences from DNA templates. In the first step 15 PCR cycles are carried out with Taq DNA polymerase in the absence of dideoxy-nucleotides in order to prepare an adequate amount of sequencing template. In a second step in which dideoxy-nucleotides and a labelled primer are added, CAS produces the sequence as well as the additional amplification of the target sequence. Two primers are used in both steps of the method.

Many DNA polymerases, including the Taq DNA polymerase, that are used in coupled DNA sequencing reactions strongly discriminates against ddNTPs and preferably incorporates dNTPs if it is furnished with a mixture of ddNTPs as well as dNTPs. In addition it incorporates each ddNTP, i.e. ddATP, ddCTP, ddGTP, ddTTP, with a strongly varying efficiency. Hence the optimization of the CAS process requires careful titration of the dideoxynucleotides.

Furthermore since coupled amplification and sequencing depends on the amount of the initial DNA, the distance between the two primers and the concentrations and the ratios of the ddNTPs and dNTPs relative to one another and to each other, the optimization of coupled amplification and sequencing reactions (CAS) requires that the reaction conditions are individually optimized for a particular DNA fragment.

All the methods described above require an interruption between the first step of exponential amplification of the template DNA and the second step for the synthesis of truncated DNA molecules and also require the individual optimization of a given DNA fragment which can be tedious and time-consuming and can lead to errors especially when sequencing a large number of different DNA molecules or when processing large amounts of samples in a hospital or laboratory or when sequencing rare samples for forensic or archaeological studies.

For this reason it would be advantageous to have available a method for sequencing nucleic acids which simultaneously potentiates the exponential amplification of molecules of full length and of molecules of truncated length in the reaction which leads to a reduction of the required amount of starting nucleic acid molecules and does not require an interruption of the exponential amplification step and of the sequencing step so that the whole reaction can be carried out more rapidly and with fewer manipulations.

SUMMARY OF THE INVENTION

The object of the present invention is to provide an improved, rapid and reliable method for sequencing DNA molecules, preferably genomic DNA.

A further object of the present invention is to provide a direct method for nucleic acid sequencing which simultaneously increases the exponential amplification of molecules of full length as well as of molecules of truncated length in the reaction which leads to a reduction of the initial amount of nucleic acid molecules that are required for the cycling reaction.

A further object of the present invention is to provide an improved, rapid and reliable method for sequencing DNA molecules, preferably genomic DNA that can be carried out in a single step in a single container.

A further object of the present invention is to provide an application according to the invention for sequence determination in medical diagnostics, forensics and population genetics.

Further objects of the invention are obvious to a person skilled in the art from the description.

In contrast to the above-described "CAS" method a DNA polymerase is used as the thermostable DNA polymerase which, compared to wild-type Taq DNA polymerase, has a reduced discrimination against the four ddNTPs in the buffer and under the conditions that are used for the thermocycling. More preferably a DNA polymerase is used which carries a "Tabor-Richardson" mutation or a functional derivative thereof which also has no 5'-3'exonuclease activity such as e.g. AmplitaqFS( (Taq DNA polymerase (-exo5'-3')(F667Y), Tabor and Richardson (1995), loc. cit.), Taquenase( (Taq DNA polymerase (235 (-exo5'-3') (F667Y), Tabor and Richardson (1995), loc. cit.) and Thermo Sequenase( (Taq DNA polymerase (-exo5'-3') (F667Y), Tabor and Richardson (1995), loc. cit.) as well as mixtures thereof or other DNA polymerases and mixtures thereof which are thermostable can also be used in the method of the present invention. Surprisingly the use of a DNA polymerase which, in comparison to wild-type Taq DNA polymerase, has a reduced discrimination against the four ddNTPs, enables the simultaneous and exponential synthesis of truncated as well as of full fragments from the start of the cycling reaction. Hence the present invention concerns a method for the direct sequencing of a nucleic acid molecule from a complex mixture of nucleic acids, such as e.g. total genomic human DNA, containing a reaction buffer, deoxynucleotides or derivatives thereof and a dideoxynucleotide or another terminating nucleotide and a thermostable polymerase which has a reduced discrimination against ddNTPs in comparison to wild-type Taq DNA polymerase. Within the sense of the present invention direct sequencing means that the nucleic acid fragment to be sequenced is simultaneously amplified and sequenced in one step without interrupting the reaction and without prior amplification of the nucleic acid fragment to be sequenced by the known methods and in such a manner that an unequivocal sequence ladder is readable.

A further difference between DEXAS and the "CAS" method described above is the principle that the initial and subsequent cycle sequencing reaction is carried out with two primers, a first primer, and a second primer which lies on the strand complementary to the first, which are preferably present in a non-equimolar ratio and serve to simultaneously produce adequate template molecules of full length as well as truncated molecules which contribute to the sequencing of the DNA molecule. Four reactions are prepared, one for the determination of each base, so that each reaction contains two primers preferably in a non-equimolar ratio to one another of which either one is labelled and the other is unlabelled or both are differently labelled. The said non-equimolar ratio between the first primer and the second primer enables the simultaneous and exponential synthesis of the truncated as well as of the full fragments from the start of the cycling reaction. Furthermore each reaction contains from the start the DNA template to be sequenced as well as a buffer solution, thermostable DNA polymerase, thermostable pyrophosphatase (optionally), the four deoxynucleotides or derivatives thereof and a dideoxynucleotide or a terminating nucleotide e.g. 3-aminonucleotide or 3'ester-derivatized nucleotides.

Thereafter cycles for denaturing and extension are carried out so that in each of these cycles two types of extension products are formed from each primer. Each primer functions such that it initiates extension products which are long enough to reach the other primer position. Simultaneously products are initiated by each primer which, due to the incorporation of a dideoxynucleotide, are terminated before the other primer position is reached. The former said products (products of full length) serve in the following cycles as a template for the production of further DNA strands of full length and are also used as templates for extensions that contribute to the sequence reaction, and the latter products (truncated products) accumulate during the cycles and contribute to the sequence ladder that is generated. Hence DEXAS results in the simultaneous exponential production of a sequencing template and a sequence ladder in a single tube without having to interrupt the thermocycling reaction.

Therefore the use of the present invention enables the DNA sequence of multicopy and single-copy regions of DNA to be determined in a single step.

Hence the present invention for the first time provides a method which enables the nucleic acid to be sequenced to be simultaneously amplified and sequenced from a complex mixture of nucleic acids, such as e.g. total genomic human DNA, without prior amplification by the known methods, in one step i.e. without interrupting the reaction and such that an unequivocal sequence ladder is readable wherein at least one thermostable DNA polymerase, a nucleic acid molecule, a first primer, a second primer, a reaction buffer, deoxynucleotides or derivatives thereof and at least one dideoxynucleotide or another terminating nucleotide is present in the initial reaction mixture.

Furthermore the aforementioned object and goals of the present invention are achieved by the provision of a method for sequencing DNA molecules in which truncated DNA molecules as well as DNA molecules of full length are simultaneously and exponentially synthesized between two positions on the said DNA molecule in a thermocycling reaction which initially contains a DNA molecule, a first primer, a second primer, a reaction buffer, a thermostable DNA polymerase, thermostable pyrophosphatase (optionally), deoxynucleotides or derivatives thereof, and a dideoxynucleotide or another terminating nucleotide thereof wherein the initial ratio of the said primers in the said thermocycling reaction is not equal to 1.

In a preferred embodiment of the method of the invention the ratio of the said primers to one another is about 2:1 to about 3:1, most preferably 2:1.

In a further preferred embodiment of the method of the invention the said primers have such a length that the signal-to-noise ratio between the specific truncated DNA molecules and the unspecific DNA molecules is large enough not to substantially prevent the reading of the sequence. The said primers preferably have a length of at least 25 nucleotides.

Primers can be synthesized by means of methods known in the state of the art. For example primers can be synthesized using known methods which do not significantly change the stability or function of the said primers during the nucleic acid sequencing method of the present invention.

Furthermore the PNA-DNA hybrid oligonucleotides (see Finn, P. J. et al., N.A.R. 24, 3357–3363 (1996), Koch, T. et al., Tetrahedron Letters, 36, 6933–6936 (1995), Stetsenko, D. A, et al., Tetrahedron Letters 37, 3571–3574 (1996), Bergmann, F. et al., Tetrahedron Letters 36, 6823–6826 (1995) and Will, D. W. et al., Tetrahedron 51, 12069–12082 (1995)) are also regarded as primers for the method according to the invention.

In a further preferred embodiment of the invention the said first primer is labelled. Moreover it is preferable that the said first primer and second primer are labelled differently. Any suitable agents or methods known in the state of the art can be used as single or differential labelling agents and methods, provided that they do not significantly change the stability or function of the said primer in the DNA sequencing method of the present invention. For example single and differential labels can be selected from the group which comprises those enzymes such as β-galactosidase, alkaline phosphatase and peroxidase, enzyme substrates, coenzymes, dyes, chromophores, fluorescent, chemiluminescent and bioluminescent labels such as FITC, Cy5, Cy5.5, Cy7, Texas-red and IRD40 (Chen et al., (1993), J. Chromatog. A 652: 355–360 and Kambara et al. (1992), Electrophoresis 13: 542–546) ligands or haptens such as e.g. biotin and radioactive isotopes such as $^{3}$H, $^{35}$S, $^{32}$P, $^{125}$I and $^{14}$C.

The method according to the invention can also be carried out as a "hot start" method. In this case it is ensured that the activity of the polymerase or polymerases only starts at an increased temperature in order to suppress a polymerization on unspecifically hybridized primers at lower temperatures. One possibility is that the thermocycling reaction additionally contains a polymerase-inhibiting agent. Polymerase antibodies are for example available commercially which only denature at higher temperatures and thus release enzyme activity of the polymerase. However, polymerases modified by genetic engineering that are present in an inactive form at lower temperatures would also be conceivable. Other polymerase-inhibiting agents are disclosed by EP 0 771 870 A1, the disclosure of which is incorporated by reference. Examples of the polymerase-inhibiting agents include acid anhydrides, such as dicarboxylic acid anhydrides (e.g. citraconic anhydride, cis-aconitic anhydride, phthalic anhydride, succinic anhydride, and maleic anhydride) and dianhydrides (e.g. pyromellitic dianhydride or naphthalenetetracarboxylic dianhydride).

DEXAS is relatively insensitive to various buffers and various deoxynucleotides and dideoxynucleotide concentrations and can be carried out using various thermostable DNA polymerases.

The number of thermocycles can be from about 18 to about 50 cycles depending on the amount of template DNA and its purity.

Buffer components which can be used can include Tris-HCl at a pH of about 9.0 to 9.5 and at a concentration of about 10 to 30 mM, ammonium sulfate at a concentration of about 10 to 20 mM preferably 15 mM, $MgCl_2$ at a concentration of about 3.5 to 5.5 mM, optionally about 0.05 mM mercaptoethanol, about 0.28% Tween20 and/or about 0.02% Nonidet 40. Buffer components, however, are not limited to these.

Deoxynucleotides may be selected from dGTP, dATP, dTTP and dCTP, but are not limited to these. According to the invention, it is additionally also possible to use derivatives of deoxynucleotides which are defined as those deoxynucleotides which are able to be incorporated by a thermostable DNA polymerase into growing DNA molecules that are synthesized in the thermocycling reaction. Such derivatives can include thionucleotides, 7-deaza-2'-dGTP, 7-deaza-2'-dATP, as well as deoxyinosine triphosphate, that can also be used as a substitute deoxynucleotide for dATP, dGTP, dTTP or dCTP, but are not limited to these. The aforementioned deoxynucleotides and derivatives thereof are preferably used at a concentration between about 300 µM and about 2 mM.

Dideoxynucleotides can be selected from ddGTP, ddATP, ddTTP and ddCTP. Dideoxynucleotides, however, are not limited to these. According to the invention, it is also additionally possible to use derivatives of dideoxynucleotides which are defined as those dideoxynucleotides that are able to be incorporated by a thermostable DNA polymerase into growing DNA molecules that are synthesized in a thermo-cycling reaction. In addition, it is also possible to use other terminating nucleotides, e.g. 3'-amino nucleotide or 3'-ester-derivatized nucleotides. Preferred concentrations of ddNTPs are between about 1 and 5 µM.

In the method according to the invention the preferred ratio of dNTPs to ddNTPs (dNTPs:ddNTPs) is between about 100:1 and 1000:1 preferably between about 300:1 and 600:1. A ratio of dNTPs to ddNTPs between about 600:1 and 1000:1 is preferred for longer nucleic acid fragments, wherein longer nucleic acid fragments means more than 0.2 kB.

In a further preferred embodiment of the method of the invention the said method is carried out at a temperature at which the signal-to-noise ratio between the specific truncated DNA molecules and the unspecific DNA molecules is large enough not to substantially impede reading of the sequence. It is less important to optimize the annealing temperature. In the case of human single-copy DNA sequences the highest possible annealing temperature drastically reduces the background. In this case the annealing and synthesis steps of the thermocycling reaction are preferably carried out at a minimum temperature of about 62° C., more preferably at about 66° C. and most preferably at at least about 68° C.

The template of the DNA molecule to be sequenced is preferably present as a total genomic DNA molecule which does not have to be cloned or purified, but this may be the case. In one embodiment of the invention the genomic DNA has a length of more than or equal to 2 kb. Other forms of DNA that can be used as templates include cloned or uncloned mitochondrial DNA, partially purified or unpurified DNA such as e.g. plasmid DNA of bacterial colonies. DEXAS functions well with about 250 ng template DNA for the determination of mitochondrial DNA sequences and about 1 µg template DNA for determining single-copy DNA sequences such as e.g. total genomic DNA, but it also functions with smaller amounts of mitochondrial or genomic DNA. The method according to the invention can also be used for the direct sequencing of unpurified single-stranded or double-stranded DNA from bacteriophages. DEXAS is in addition relatively independent of the base composition of the template.

The method according to the invention can especially be used for the direct sequencing of nucleic acid molecules in a Complex Mixture. Complex Mixtures are nucleic acid mixtures in which no enriching purification for the target nucleic acid molecule has been performed. However, the nucleic acid may have been isolated from its original source, e.g. cells. In Complex Mixtures, the ratio of the total number of nucleotides in the target nucleic acid molecule and in the background nucleic acid molecules is substantially smaller than one and the ratio of the number of the target nucleic acid molecule to the number of the background nucleic acid molecules is not greatly larger than one, or even smaller than one, and possibly even substantially smaller than one. For instance, the ratio of the number of the target nucleic acid molecule to the number of the background nucleic acid molecules can range from about 0.0001 to about 1. Such Complex Mixtures can be a whole human genomic DNA containing a single copy of a human gene (e.g. CCR-5 gene) as the target DNA molecule for direct sequencing by the method of the invention. Table 1c shows an example of the Complex Mixture.

The method according to the invention can also be used for the direct sequencing of nucleic acid molecules in a Medium Complex Mixture. Medium Complex Mixtures are nucleic acid mixtures in which no enriching purification for the target nucleic acid molecule has been preformed. However, the nucleic acid may or may not have been isolated from its original source, e.g. bacterial cells. In Medium Complex Mixtures, the ratio of the total numbers of nucleotides in the target nucleic acid molecule and in the background nucleic acid molecules is close to or smaller than one and the ratio of the number of the target nucleic acid molecule to the number of the background nucleic acid molecules is larger than one. For instance, the ratio of the number of the target nucleic acid molecule to the number of the background nucleic acid molecules can range from about 1 to about 1,000. Such Medium Complex Mixtures can be DNA from a bacterial colony (containing plasmid DNA as the target DNA molecule), DNA from phage plaques (containing M 13 DNA as the target DNA molecule), or partially purified or unpurified mitochondrial DNA. Table 1b shows an example of the Medium Complex Mixture.

The method according to the invention can also be used for the direct sequencing of template nucleic acid molecule in a Non-Complex Mixture. Non-Complex Mixtures are nucleic acid mixtures in which the template nucleic acid has been amplified and/or purified or partially purified. The amplification and purification methods can be cloning with subsequent plasmid purification, gradient centrifugation and purification, or the product of PCR in which the PCR product may or may not be purified (the number of PCR cycles in the absence of terminating nucleotides may range from 1 to 50). In Non-Complex Mixtures, the ratio of the number of the target nucleic acid molecule and the number of background nucleic acid molecules is much larger than one. For instance, the ratio of the number of the target nucleic acid molecule to the number of the background nucleic acid molecules can range from about 1,000 to about $1 \times 10^{18}$. Table 1a shows an example of the Non-Complex Mixture.

In a preferred embodiment the method according to the invention is furthermore characterized in that each thermocycling reaction to determine the position of A, G, C and T in the said DNA molecule is carried out in a single step, in a single container, vessel or tube.

The method according to the invention can be used for direct sequencing of RNA, such as human RNA. In this case, the polymerase exhibits, in addition to the reduced ability to discriminate against ddNTP's, reverse transcriptase activity. One example of the polymerase which can be used for direct sequencing of RNA, such as human RNA, is a polymerase obtained from Thermus thermophilus Tth, which exhibits reverse transcriptase activity (Meyers, T. W., Gelfand, D. H. (1991) Biochemistry 30 (31): 7661–7666) and which additionally carries a Tabor-Richardson mutation (F667Y) or a functional derivative thereof.

In a preferred embodiment of the method of the invention, the nucleic acid molecule to be sequenced can be present in the form of RNA. To sequence a RNA with this embodiment of the method of the invention, at least two activities must be present in one polymerase enzyme: such an enzyme may be a DNA polymerase, for example, containing a Tabor-Richardson (F667Y) mutation, or a functional derivative thereof, which leads to a DNA polymerase enzyme, such as ThermoSequenase, that has a low rate of discrimination against ddNTPs. A second activity must be present in the polymerase enzyme enabling reverse transcription of RNA into DNA. Taq DNA polymerase (Jones et al., Nucl. Acids Res. 17: 8387–8388 (1989)) or Tth DNA polymerase (Myers et al., Biochemistry 30:7666–7672 (1991)) may be used. Tth polymerase reverse transcribes the RNA template into DNA which may then be utilized by the same enzyme as a template for the sequencing reaction. Since Tth is a homologue of Taq, the F667Y-mutation may be incorporated into the enzyme leading to a low discrimination against ddNTPs and thus all activities required for the above reaction, namely DNA polymerase activity, the ability to incorporate ddNTPs well and reverse transcriptase activity can be present in the same enzyme.

Suitable buffers include those reported in Myers et al (1991) Biochemistry 30:7666–7672. The following buffer can be used for the reaction ensuring the function of the activities in case the enzyme requires the presence of Mn ions: 10 mM Tris-HCl (pH 8.3), 40 mM KCl, 1 mM $MnCl_2$. The reaction buffer may initially optionally contain $MgCl_2$ at about 1 to 5 mM for reverse transcription. Reverse transcription is accomplished by performing an incubation step for 15 minutes at 70° C. Subsequently the $MgCl_2$ concentration is adjusted to between 1 mM and 5 mM and sequencing reaction is performed.

In a more preferred embodiment, the method for the direct exponential amplification and sequencing of a nucleic acid starting from RNA is performed in a single step, in a single container, vessel or tube for each thermocycling reaction to determine the position of each nucleotide in the RNA molecule.

In a preferred embodiment of the invention, a DNA polymerase from Carboxydothermus hydrogenoformans is used. This enzyme disclosed in EP 0 834 569 has reverse transcriptase activity in the presence of Mg ions without the presence of Mn ions. In a preferred embodiment of the invention the polymerase is mutated as described in Tabor and Richardson (Tabor, S. & Richardson, C. C. (1995) Proc. Natl. Acad. Sci. USA 92, 6339–6343; EP 0 655 506) in order to create an enzyme that does not discriminate against ddNTPs. In this set-up Mg is present from the beginning in a range between about 0.5 mM and 20 mM, no extra Mn is required. A suitable buffer additionally may comprise, but is not limited to, Tris-HCl (pH 6.5 to 11), KCl (2mM–100 mM), ammoniumsulphate (2mM–100 mM) and additional enzymes, such as thermostable pyrophosphatase (0,1–50 U). In addition, at least one nucleotide must be present. The reactions are cycled as disclosed above. The enzyme thus contains all activities to perform the reactions of reverse transcription, amplification and sequencing.

Suitable sources of nucleic acid molecules in the method according to the invention are body fluids such as sperm, urine, blood or fractions of these, hairs, an individual cell, cells or fractions thereof, hard tissue such as bones or soft tissue or fractions thereof and cell cultures or fractions thereof.

The present invention also serves for the application of the method according to the invention for the determination of a nucleotide sequence of a given nucleic acid molecule e.g. for sequencing Shotgun libraries with two labels for large-scale genome projects and in medical diagnostics, forensics and population genetics. The method of the present invention can be used to detect genetic mutations or polymorphisms, to identify the origin of the sequenced nucleic acid or to detect the presence of foreign or infectious agents in a sample.

The present invention relates to all combinations of all procedures of the above methods.

After preparation the sequencing reactions can be loaded directly onto a sequencing gel such as e.g. after addition of a commonly used application buffer (e.g. formamide which contains 20 mM EDTA (pH 7.4) and 6 mg/ml dextran blue) and denaturation (e.g. for 4 minutes at 96° C.). The sequence ladder can be read according to known methods. The method of the invention is well suited for automation. Since the two primers in the reaction are provided with different labels which can for example be detected with two different wavelengths, the method of the present invention enables the simultaneous sequencing of both strands of a template and the detection of both reactions in one or several gel lanes. In general many DEXAS reactions that are carried out using different dyes can be carried out simultaneously in the same tube and applied to a sequencing instrument that is equipped with several lasers or be detected by other methods such as e.g. autoradiography.

A further subject matter of the present invention is a kit for the direct sequencing of a nucleic acid molecule from a complex mixture of nucleic acids, such as e.g. total genomic human DNA, containing a reaction buffer, deoxynucleotides or derivatives thereof and a dideoxynucleotide or a further terminating nucleotide and a thermostable polymerase which has a reduced discrimination against ddNTPs compared to wild-type Taq DNA polymerase. Within the sense of the present invention direct sequencing means that the nucleic acid fragment to be sequenced is simultaneously amplified and sequenced, without prior amplification of the nucleic acid fragment to be sequenced by the known methods, in a single step without interrupting the reaction and such that an unequivocal sequence ladder can be read.

A further subject matter of the present invention is a kit for the direct sequencing of a nucleic acid molecule of a complex mixture of nucleic acids containing a reaction buffer, deoxynucleotides or derivatives thereof and a dideoxynucleotide or another terminating nucleotide, a thermostable polymerase and two primers whose ratio is larger than 1. The kit particularly preferably contains a thermostable polymerase which has a reduced discrimination against ddNTPs in comparison to the wild-type Taq DNA polymerase.

SHORT DESCRIPTION OF THE FIGURES

FIG. 1 Schematic representation of DEXAS. Two oligonucleotides (27mers), either a labelled and an unlabelled oligonucleotide or an oligonucleotide labelled with FITC and an oligonucleotide labelled with Cy5 (ratio 2:1) are mixed in four tubes with human genomic DNA (250 ng to 3 μg), a heat-resistant DNA polymerase, the four deoxynucleotides and in each case one of the dideoxynucleotides. Cycles for denaturing and subsequent annealing and extension are carried out. During each extension the primers are either extended up to the complementary primer position or they are interrupted by the incorporation of a dideoxynucleotide. In subsequent cycles these former products serve as templates for the further generation of products of full length as well as for the termination reactions whereas the latter products accumulate during all of the cycles that are carried out and contribute to the sequence signal. After the cycling the reactions are denatured and, depending on their label, are either analysed on an A.L.F. or an A.L.F. express.

Figure 2:
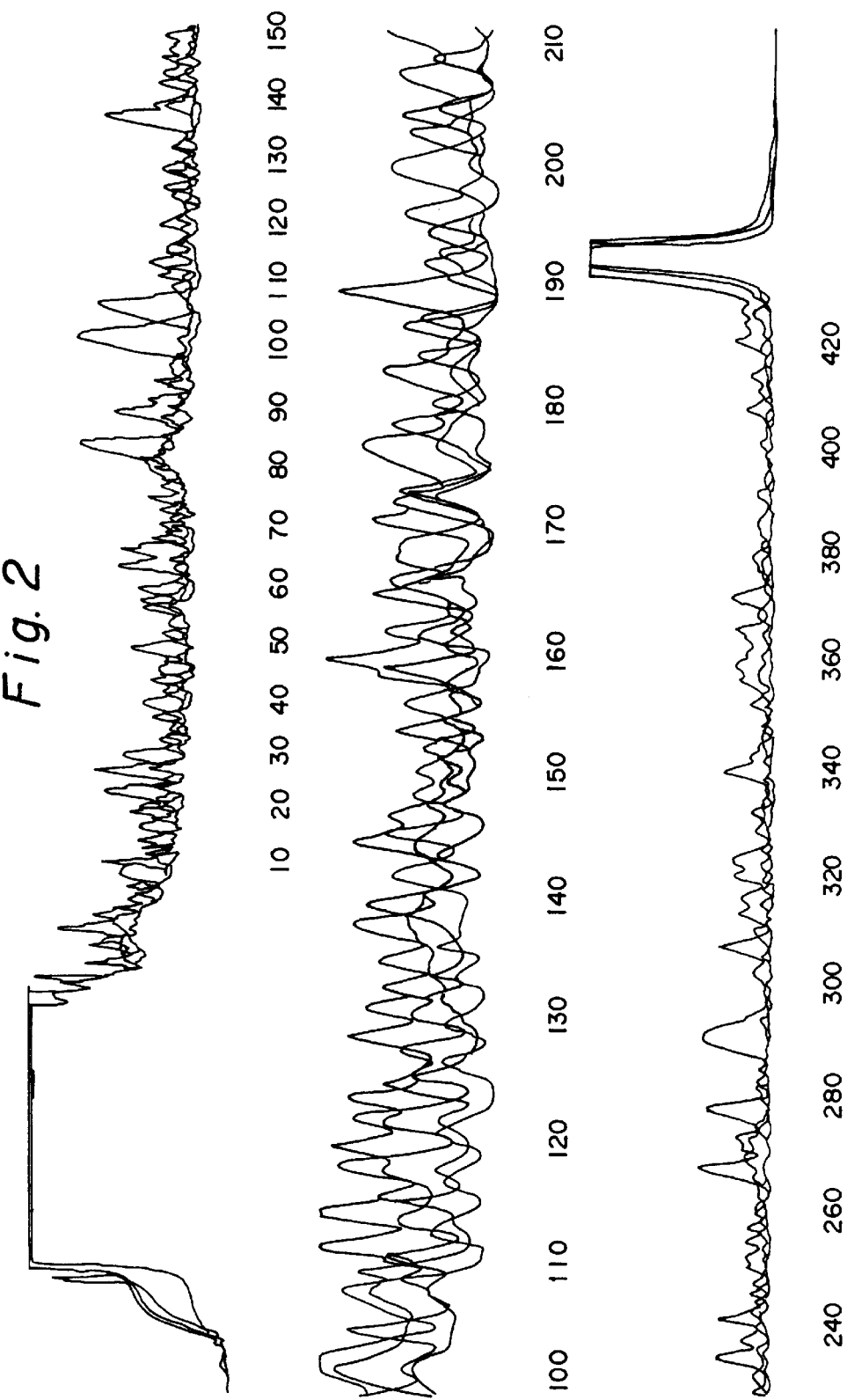

FIG. 2. DEXAS reaction carried out on a 521 bp segment of the human mitochondrial control region. Eight pmol of an FITC-labelled (mtDNA1-L16026) and 4 pmol of an unlabelled primer (mtDNA2-H16498) were used together with 250 ng of total genomic human DNA (see text for details). A strong signal can be seen before the first processed base and a strong stop can be seen at about base number 440. The sequence was processed with the A.L.F. software and was not edited manually. A total of 433 bases was determined.

Figure 3A:
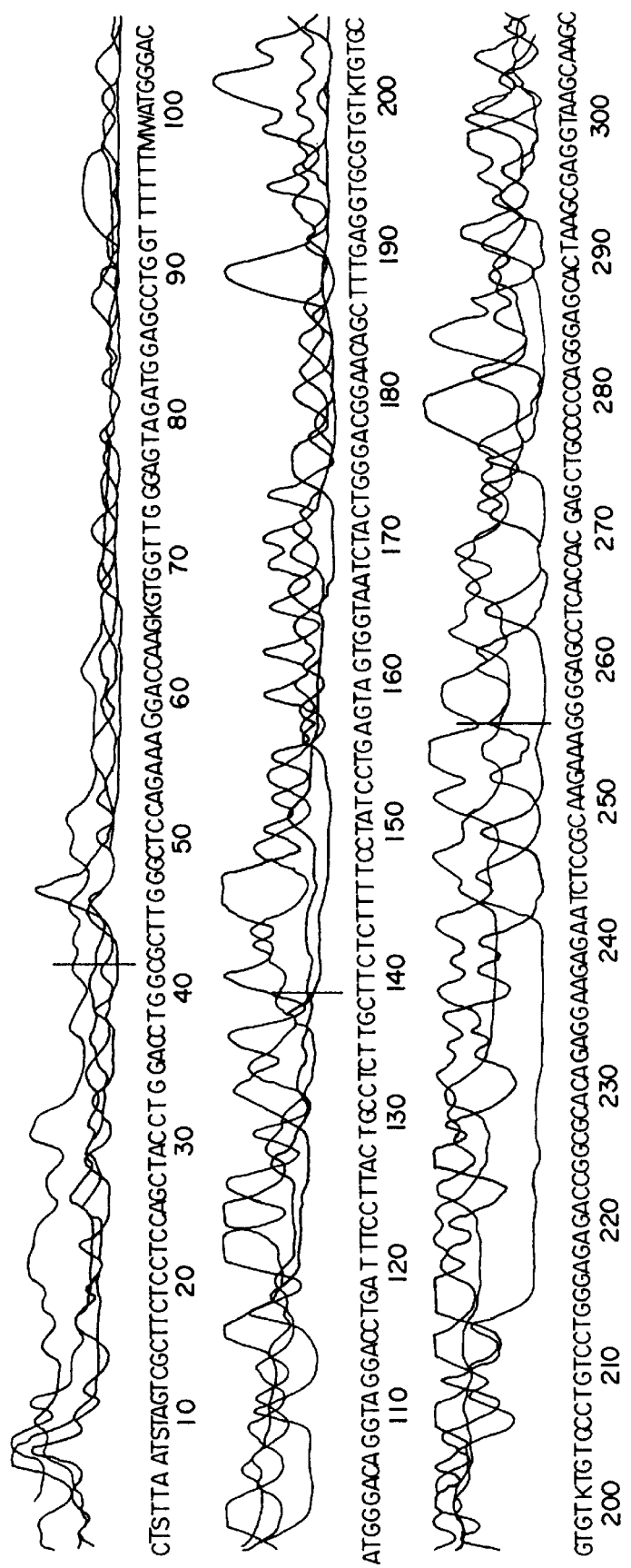
Figure 3B:
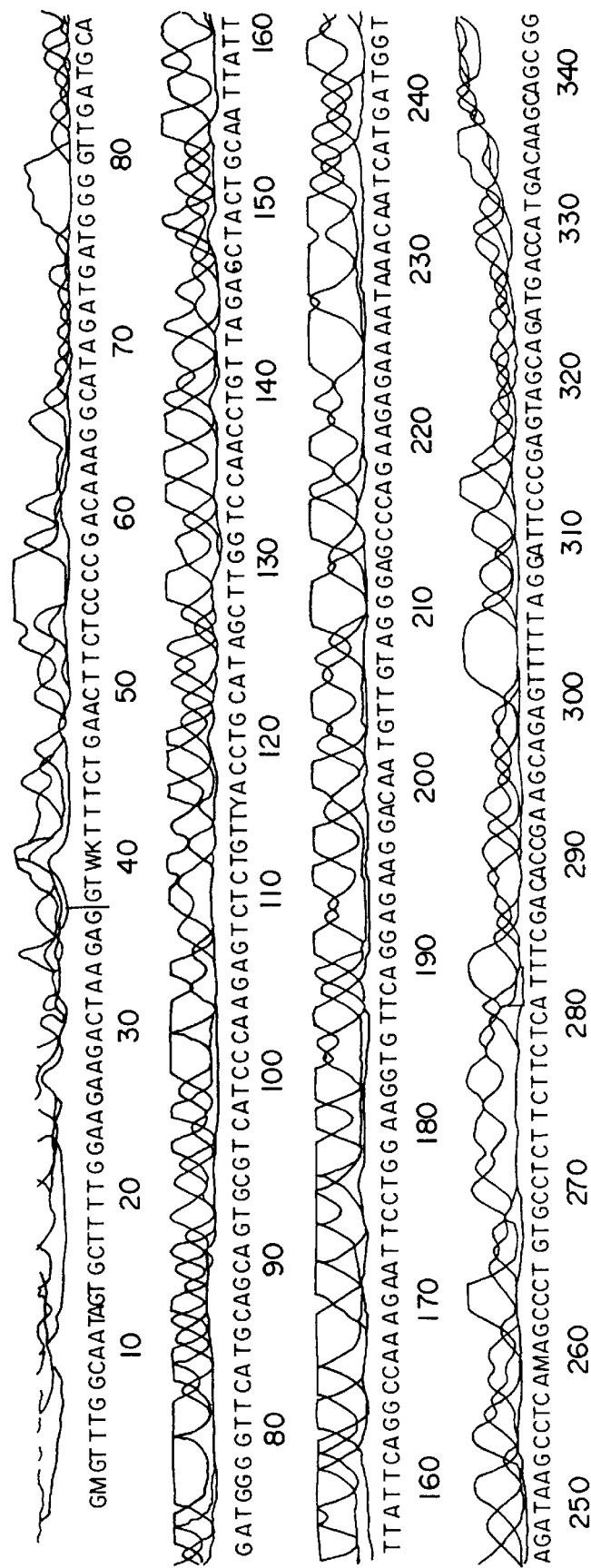

FIGS. 3A & 3B DEXAS reaction carried out on a single-copy genes. FIG. 3A shows a sequence of the human p53 gene (SEQ ID NO: 7) whereas FIG. 3B shows a sequence of the human CCR-5 gene (SEQ ID NO: 8) (see text for details). The sequence was processed with the A.L.F. software and was not edited manually. A total of 305 bases was determined in the case of the p53 gene whereas 343 bases were determined for the CCR-5 gene.

Figure 4:
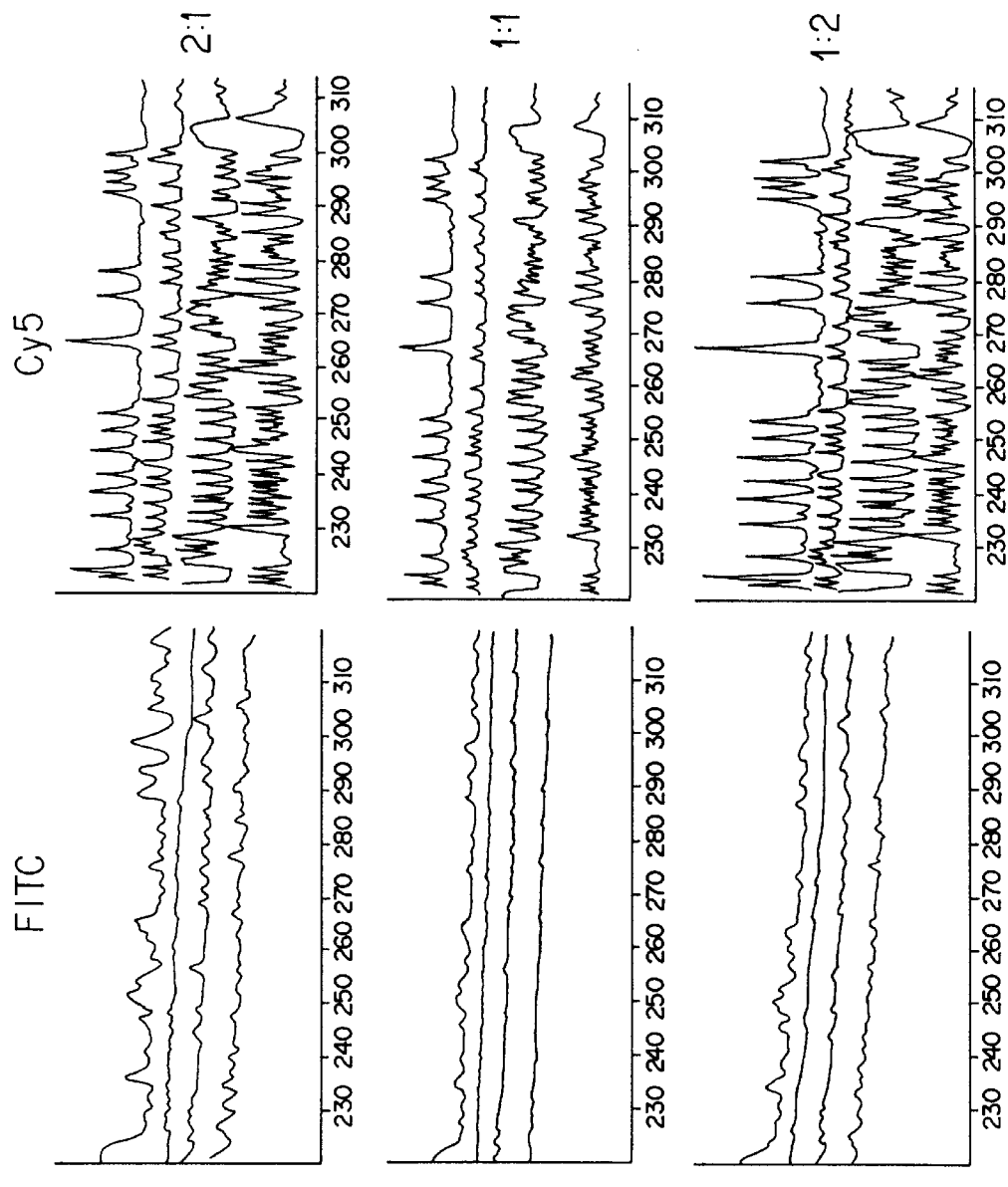

FIG. 4. Two colour DEXAS reaction using different oligonucleotide ratios. Each of the reactions was carried out using 250 ng genomic human DNA and a total amount of 12 pmol primer. MtDNA1 was labelled with FITC (left panel) and MtDNA2 was labelled with Cy5 (right panel). The ratios between FITC-MtDNA1 and Cy5-MtDNA2 were varied between 2:1 (upper panel), 1:1 (middle panel) and 1:2 (lower panel). The largest signal-to-noise ratio for both primers is achieved when a ratio of 2:1 is used. The raw data of the A.L.F. and of the A.L.F. express instruments are shown. The assignment of the base signals from top to bottom is C, A, G, and T respectively.

Figure 5:
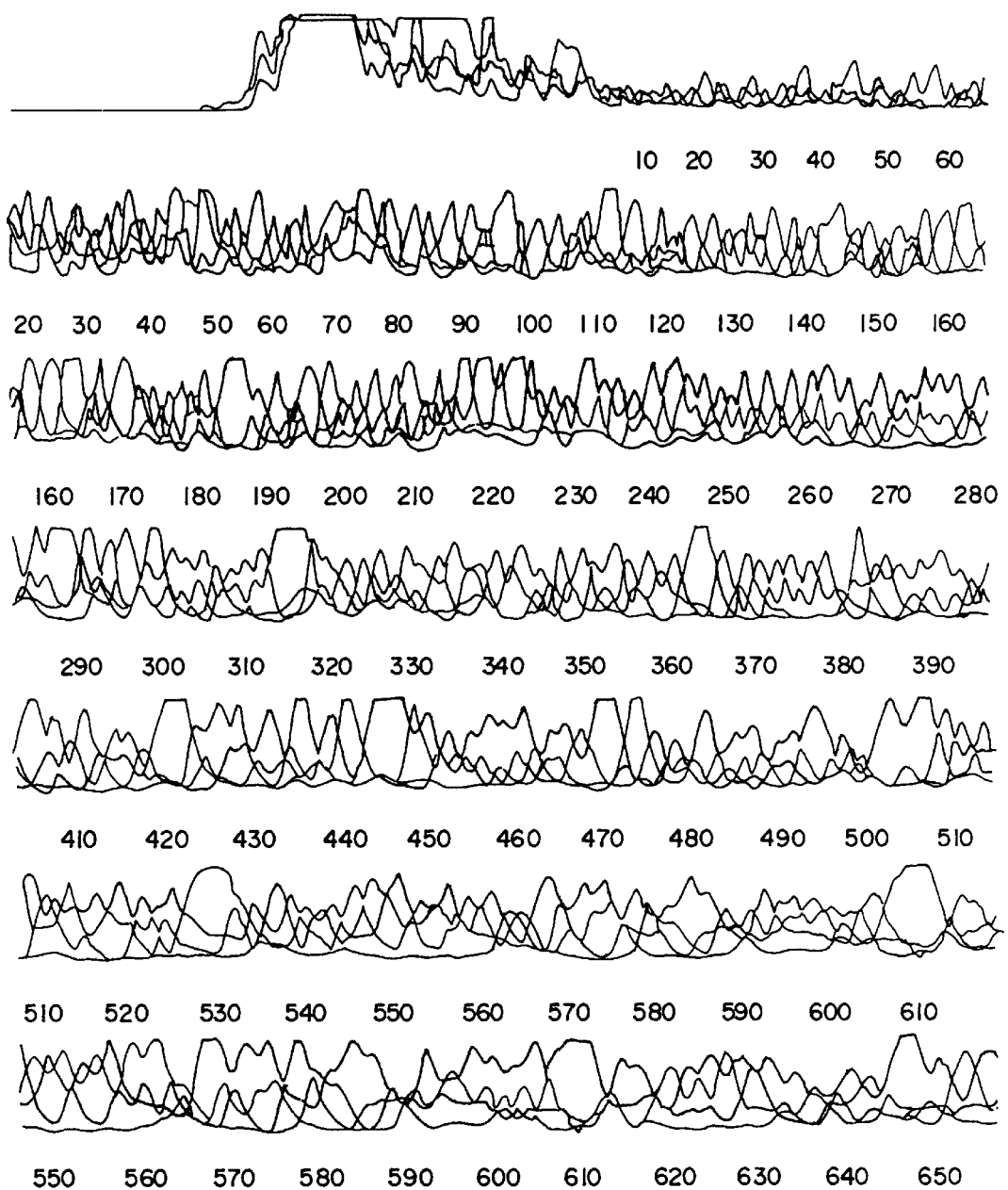

FIG. 5. DEXAS was carried out using simultaneously a fluorescein-labelled 'T3' primer and a Cy5-labelled 'universal' primer. The figure shows the sequence that was obtained with the Cy5-labelled primer. The two primers were used in a single reaction using one bacterial colony. 4 μl of each was analysed on an A.L.F. or an A.L.F. express. The reaction with the 'T3' primer yielded 407 bases and the reaction with the 'universal' primer yielded 668 bases.

FIG. 6. The insert of a plasmid was sequenced from both sides in a reaction using a FITC-labelled (SEQ ID NO: 10) 'T3' primer and an opposite Cy5-labelled (SEQ ID NO: 9) 'universal' primer. The simultaneous use of two differently labelled oligonucleotides in a DEXAS reaction allowed the 548 base insert to be sequence without leaving ambiguous positions. The primers were positioned at a distance of 670 bp to one another.

DETAILED DESCRIPTION OF THE INVENTION

The invention is described in more detail by the following non-limiting examples.

EXAMPLE 1

Template Preparation

Total genomic human DNA was prepared from 2 ml blood samples using a rapid cleaning kit (Cambridge Molecular Technologies Ltd., Cambridge, UK). Purified DNA was diluted in ddH$_2$O to a concentration of 175 ng per μl.

Sequencing Reagents and Conditions

Unlabelled and FITC-labelled oligonucleotides were synthesized with an ABI DNA/RNA synthesizer model 392. Cy5-labelled oligonucleotides were obtained from the Pharmacia Biotech Company (Freiburg, Germany). The following oligonucleotides were used in each case to sequence the mitochondrial control region (mtDNA), the p53 gene (p53) and the CCR-5 gene (CCR-5):

SEQ ID NO. 1:
(mtDNA1-L16026): 5'-GAT TCT AAT TTA AAC TAT TCT CTG TTC-3';
SEQ ID NO. 2:
(mtDNA2-H16498): 5'-TTA TGA CCC TGA AGT AGG AAC CAG ATG-3';
SEQ ID NO. 3:
(p53-1/exon-7):5'-GGA GGC ACT TGC CAC CCT GCA CAC TGG-3';
SEQ ID NO. 4:
(53-2/intron-8):5'-CTC CTC CAC CGC TTC TTG TTC TGC TTG-3'
SEQ ID NO. 5:
(CCR5-1):5'-GGC TGG TCC TGC CGC TGC TTG TCA T-3';
SEQ ID NO. 6:
(CCR5-2):5'-CTG CTC CCC AGT GGA TCG GGT GTA AAC-3'.

The numbering of the mtDNA primers refers to the 3' end according to Anderson et al. (1981) (Nature 290, 457–465) and L and H refer to the L strand and the H strand respectively. The DEXAS reaction was carried either using ThermoSequenase( (Tabor, S. and Richardson, C. C. (1995) Proc, Natl. Acad. Sci. USA 92, 6339–6343) (Amersham, UK) reagents or using the following 10 x buffer: 500 mM Tris-HCl (pH 9.2), 160 mM (NH$_4$)$_2$SO$_4$, 35 mM MgCl$_2$ (ScienTech Corp., St. Louis, Mo.). Three different nucleotide mixtures were evaluated for the termination: (i) 1:333, 1 mM dATP, 1 mM dCTP, 1 mM dGTP, 1 mM dTTP, in which the A, C, G and T reaction each contained 3 μM of the corresponding dideoxy-nucleotide. (ii) 1:666 also containing in each case 1 mM of each deoxynucleotide but 1.5 μM of the corresponding dideoxynucleotide. (iii) 1:1000 also containing in each case 1 mM of each deoxynucleotide but 1.0 μM of the corresponding dideoxynucleotide. All termination mixtures were prepared using 50 mM Tris-HCl (pH 9.2), 16 mM (NH$_4$)$_2$SO$_4$, 5 mM MgCl$_2$.

A premix of 1 µl (units not defined) Taquenase( (ScienTech Corp., St. Louis, Mo.) and 1 unit thermostable pyrophosphatase (NEB, Beverly, Mass.) was prepared for each sequencing reaction. In the case of the ThermoSequenase reactions, the reactions were prepared as recommended by the manufacturer. In the other cases a 20 µl mixture of primer (2 pmol to 12 pmol), DNA (15 ng to 1.5 µg), sequencing buffer (2 µl of the 10× buffer, see above) and enzyme was prepared and a 5 µl aliquot of this was added to 2 µl termination mix. The sequencing reactions were carried out in a thermocycler with a heatable cover (MJ-Research, Watertown, Mass.). The reactions were stopped by adding 5 µl formamide (20 mM EDTA (pH 7.4) and 6 mg/ml dextran blue) which was followed by a 4 minute denaturation at 95° C.

The sequencing reactions were analysed on an A.L.F. when FITC-labelled primers were used and on an A.L.F. express when Cy5-labelled primers were used (both Pharmacia Biotech, Uppsala, Sweden). HydroLink Long Ranger( (FMC, Rockland, Me.) gels and 30 cm glass plates were used in all cases. The gel conditions were in accordance with the manufacturer's recommendations.

EXAMPLE 2

DEXAS of mitochondrial DNA sequences

Two oligonucleotides were synthesized both having a length of 27 nucleotides which span a 521 base pair region of the human mitochondrial control region. 27-mers were used to minimize an unspecific annealing of the primers to incorrect priming positions and to enable the reaction temperatures to remain above 62° C. during all synthesis steps. One of the two oligonucleotides was labelled at the 5' end with fluorescein (mtDNA1) whereas the other (mtDNA2) was unlabelled. 4 pmol of each of the primers was mixed with ThermoSequenase( (Amersham, UK) reagent which contained enzyme (DNA polymerase and thermostable pyrophosphatase), reaction buffer and a mixture of deoxynucleotides and dideoxynucleotide. Different amounts of human DNA (500 ng, 250 ng, 125 ng, 62 ng, 0 ng) were added to individual aliquots of this mixture. 500 ng template DNA but no unlabelled primer was added to one tube. The reactions were incubated for 3 minutes at 95° C. in order to enable a complete denaturation of the template DNA. Subsequently 35 cycles each of 30 sec. at 62° C. and 40 sec. at 95° C. were carried out. The reactions were stopped and denatured by the addition of formamide and heating to 95° C. for 4 min before they were loaded onto an A.L.F. sequencing gel.

In the case were no DNA had been added no sequence was detectable. No sequence was detectable when only the labelled primer and no unlabelled primer had been added. However, sequence curves were obtained in cases in which 62 ng or more template had been used. In the reactions in which 250 ng and 500 ng had been used the A.L.F. software was able to determine more than 400 bases.

Using a constant amount of template DNA of 500 ng and a total amount of 12 pmol of the two primers, the ratios between the labelled primer and the unlabelled primer were varied in each case between 3:1, 2:1, 1:1, 1:2 and 1:3. The reaction in which the primers were present in equimolar amounts yielded poor signals whereas all other ratios, independently of whether the labelled or the unlabelled primer was present in excess, yielded better results. The ratios 2:1 and 1:2 yielded the best results. It was surprising and unexpected that both non-equimolar ratios are advantageous. Using 8 pmol of the primer mtDNA1 and 4 pmol of the primer mtDNA2 we presently routinely determine 450 base pairs of the mitochondrial control region.

The ratio of the deoxynucleotides (dNTPs) to dideoxynucleotides (ddNTPs) can be varied in the DEXAS reaction. A higher proportion of dNTPs will probably allow an increased template production in each cycle whereas a higher proportion of ddNTPs would lead to an increased termination of the extension products before the priming position of the second unlabelled primer is reached. The latter products will contribute to the sequence reaction but not to the further template amplification. In order to determine to what extent the ratio of ddNTPs to dNTPs influences the reaction, ddNTPs were mixed with dNTPs in ratios of 1:333, 1:666 and 1:1000 and used in a DEXAS reaction containing 8 pmol of an FITC-labelled primer (mtDNA1), 4 pmol of an unlabelled primer (mtDNA2) and 300 ng human DNA. The reaction conditions were as described above. The results showed that the ratio 1:666 (ddNTPs:dNTPs) yielded stronger signals.

EXAMPLE 3

DEXAS of Single Copies of Human DNA Sequences

In order to evaluate the applicability of DEXAS to single-copy DNA sequences, primers were synthesized which flank a 507 base pair segment of the intron 7 and the exon 8 of the human p53 gene. DEXAS reactions were prepared which each contained 8 pmol of an FITC-labelled sequencing primer (p53-1), 4 pmol of an unlabelled (p53-2) primers and 3.5 µg, 1.75 µg, 875 ng and 430 ng human DNA. These reactions were denatured for 3 minutes at 95° C. and 40 cycles comprising 30 seconds at 62° C. and 40 seconds at 95° C. were carried out. The results showed a clearly readable sequence. In order to improve the results various modifications of the protocol were evaluated. The annealing temperature was increased and the amount of the sequencing primer was reduced. Additionally the number of cycles was increased to 47 and various primer ratios and template concentrations were evaluated. The best results were obtained using 8 pmol of the FITC-labelled primer and 4 pmol of the unlabelled primer and cycling temperatures of 30 seconds at 68° C. and 30 seconds at 95° C. These conditions yielded between 260 and 320 bases of the sequence with 1 to 5 ambiguities per reaction in five experiments (FIG. 3A). If about 1 µg or more template was used, the sequence signals were read with the A.L.F. software using automated processing.

In order to further evaluate the general applicability of DEXAS to single copy genes, primers were synthesized which flank a 382 base pair segment of the CCR-5 gene. 3_pmol of the CCR5-1, 6 pmol of the FITC-labelled primer CCR5-2, 0.5–1.0 µg template DNA and 45 cycles DEXAS were used. In the sequence reactions carried out on 40 samples the reading lengths varied between 230 bp and 351 bp (average 294 bp). A typical reaction is shown in FIG. 3B.

EXAMPLE 4

Simultaneous Sequencing of Both DNA Strands

It was shown that it is possible to sequence both complementary DNA strands of plasmid DNA in a single reaction using two different fluorescently-labelled primers (Wiemann, S., et al., (1995) *Analytical Biochemistry* 224, 117–121). The applicability of this approach to DEXAS was analysed using an FITC-labelled primer (mtDNA1), a Cy5-labelled primer (mtDNA2) and 500 ng human DNA as the template. While retaining the above reaction conditions the primer ratios were varied (FITC-mtDNA1:Cy5-mtDNA2) (3:1, 2:1, 1:1, 1:2 and 1:3). After the cycling reaction and denaturation 5 µl of the reaction was applied to an A.L.F. or an A.L.F. express instrument. As in previous experiments considerably poorer results were obtained if equimolar amounts of primer were used compared to reactions in which non-equimolar amounts were used (FIG. 4). A ratio of 2:1 at a total amount of 12 pmol gave the best signal-to-noise ratio. In such reactions 450 bases were read on both strands without yielding ambiguous positions. The observation that a larger amount of FITC-labelled primer than Cy5-labelled primer is advantageous is probably due to experiments it was possible to show that the two colour approach can also be applied to single-copy the better signal-to-noise ratio of Cy5 compared to FITC. In further genes.

TABLE 1a

Non-Complex Mixtures

| A: Size | A: Number of Molecules | A: Total Number of Nucleotides |
|---|---|---|
| 1000 bp | $1 \times 10^9$ | $1 \times 10^{12}$ |
| B: Size | B: Number of Molecules | B: Total Number of Nucleotides |
| $3 \times 10^6$ bp | 1000 | $3 \times 10^9$ |
| Ratio of Number of Molecules (A:B) | Ratio of Total Number of Nucleotides (A:B) | |
| $1 \times 10^6$ | 333 | |

"A" is a target DNA molecule in a PCR product.
"B" represents background DNA molecules in the PCR product.

TABLE 1b

Medium Complex Mixtures

| A: Size | A: Number of Molecules | A: Total Number of Nucleotides |
|---|---|---|
| 1000 bp | 300 | $3 \times 10^5$ |
| B: Size | B: Number of Molecules | B: Total Number of Nucleotides |
| $3 \times 10^6$ bp | 1 | $3 \times 10^6$ |
| Ratio of Number of Molecules (A:B) | Ratio of Total Number of Nucleotides (A:B) | |
| 300 | 0.1 | |

"A" is a target DNA molecule in the DNA from a colony of bacterial cells.
"B" represents background DNA molecules in the DNA from the colony of bacterial cells.

TABLE 1c

Complex Mixtures

| A: Size | A: Number of Molecules | A: Total Number of Nucleotides |
|---|---|---|
| 1000 bp | 1 | 1000 |
| B: Size | B: Number of Molecules | B: Total Number of Nucleotides |
| $3 \times 10^9$ bp | 1 | $3 \times 10^9$ |
| Ratio of Number of Molecules (A:B) | Ratio of Total Number of Nucleotides (A:B) | |
| 1 | $3 \times 10^{-6}$ | |

"A" is an allele or a single copy of a human gene as a target DNA molecule in a human genomic DNA.
"B" represents background DNA molecules in the human genomic DNA.

What is claimed is:

1. A method for sequencing at least a portion of a RNA involving converting said RNA into a DNA and simultaneously amplifying said DNA and generating truncated copies of said DNA for sequencing, comprising the steps of
(a) subjecting a mixture A to conversion of said RNA to said DNA and, in a single step, to DNA amplification and generation of truncated copies of said DNA by subjecting the mixture A to a thermocycling reaction, the thermocycling reaction comprises heat denaturation, annealing and synthesis, wherein said mixture A comprises said RNA,
a first primer which is able to hybridize with a strand of said DNA, a second primer which is able to hybridize with a strand of DNA complementary to the strand with which the first primer is able to hybridize, wherein at least one of the first and second primers is labelled,
a reaction buffer,
deoxynucleotides or deoxynucleotide derivatives, wherein said deoxynucleotide derivatives are able to be incorporated by a thermostable DNA polymerase into growing DNA molecules in place of one of dATP, dGTP, dTTP or dCTP,
at least one dideoxynucleotide or another terminating nucleotide, and
a thermostable DNA polymerase having a reduced, compared to wild-type Taq DNA polymerase, discrimination against the incorporation of dideoxynucleotides relative to deoxynucleotides, wherein said thermostable DNA polymerase has (1) a Tabor-Richardson mutation, or a functional derivative thereof, and (2) reverse transcriptase activity, to simultaneously make full-length and truncated copies of said DNA, wherein the full-length copies have a length equal to that of at least a portion of said DNA spanning the binding sites of the first and second primers;
(b) separating at least the truncated copies of said DNA to obtain a sequence ladder; and thereafter
(c) reading the sequence ladder to obtain the sequence of said at least a portion of said RNA.

2. The method of claim 1, wherein the deoxynucleotide derivatives are thionucleotides, 7-deaza-2'-dGTP, 7-deaza-2'-dATP or deoxyinosine triphosphate.

3. The method of claim 1, wherein said another terminating nucleotide is 3'-aminonucleotide or a nucleotide having an ester group at the 3'position.

4. The method of claim 1, wherein said thermostable DNA polymerase is a Taq DNA polymerase lacking 5'-3'exonuclease activity.

5. The method of claim 1, wherein said thermostable DNA polymerase is Taq DNA polymerase, Tth DNA polymerase, Tfl DNA polymerase or a DNA polymerase from Carboxydothermus hydrogenoformans having a Tabor-Richardson mutation, or a functional derivative of the Tabor-Richardson mutation.

6. The method of claim 1, wherein said thermostable DNA polymerase is Tth DNA polymerase having a Tabor-Richardson mutation, or a functional derivative of the Tabor-Richardson mutation.

7. The method of claim 1, wherein the thermocycling reaction in step (a) is carried out without interruption in a single container, vessel or tube.

8. The method of claim 1, wherein the initial molar ratio of said first primer to said second primer is not equal to 1:1 in step (a).

9. The method of claim 8, wherein the initial molar ratio of said first primer to said second primer is about 2:1 to about 3:1 in step (a).

10. The method of claim 9, wherein the initial molar ratio of said first primer to said second primer is about 2:1 in step (a).

11. The method of claim 1, wherein the first and second primers are differently labelled.

12. The method of claim 1, wherein the first and second primers independently have a length of at least 25 nucleotides.

13. The method of claim 1, wherein the initial ratio of said deoxynucleotides and deoxynucleotide derivatives to said dideoxynucleotide and another terminating nucleotide in mixture A is between about 100:1 and about 1000:1.

14. The method of claim 13, wherein the initial ratio of said deoxynucleotides and deoxynucleotide derivatives to said dideoxynucleotide and another terminating nucleotide in mixture A is between about 300:1 and about 600:1.

15. The method of claim 1, wherein the initial concentrations of said deoxynucleotides or deoxynucleotide derivatives in mixture A are between about 300 $\mu$M and about 2 mM.

16. The method of claim 1, wherein the initial concentration of said dideoxynucleotide or another terminating nucleotide in mixture A is between about 1 and about 5 $\mu$M.

17. The method of claim 1, wherein mixture A further comprises at least one thermostable pyrophosphatase.

18. The method of claim 1, wherein the annealing and synthesis of the thermocycling reaction are carried out at a temperature of at least about 66° C.

19. The method of claim 18, wherein the annealing and synthesis of the thermocycling reaction are carried out at a temperature of at least about 68° C.

20. The method of claim 1, wherein said RNA in mixture A is obtained from a body fluid, hairs, an individual cell, cells or fractions thereof, a tissue or fractions thereof, a cell culture or fractions thereof, a tissue culture or fractions thereof, a bacteria or a virus.

21. The method of claim 1, wherein said RNA in mixture A is an RNA in a complex mixture of nucleic acids.

22. The method of claim 1, wherein said RNA in mixture A is an RNA mixed with total genomic DNA.

23. The method of claim 22, wherein said total genomic DNA is unpurified.

24. The method of claim 1, wherein said RNA in mixture A is unpurified RNA.

25. The method of claim 1, wherein said RNA in mixture A is RNA from single copy genes.

26. The method of claim 1, wherein mixture A further comprises at least one polymerase-inhibiting agent against said thermostable DNA polymerase, which polymerase-inhibiting agent loses inhibitory ability, thereby allowing said thermostable DNA polymerase to be active, at a temperature which is at least the temperature at which unspecifically hybridized primers separate from a DNA molecule.

27. The method of claim 26, wherein said at least one polymerase-inhibiting agent is a compound containing at least one acid anhydride group per molecule.

28. The method of claim 27, wherein said at least one polymerase-inhibiting agent is citraconic anhydride, cis-aconitic anhydride, phthalic anhydride, succinic anhydride, or maleic anhydride.

29. The method of claim 27, wherein said at least one polymerase-inhibiting agent is a compound having at least two acid anhydride groups per molecule.

30. The method of claim 27, wherein said at least one polymerase-inhibiting agent is pyromellitic dianhydride or naphthalenetetracarboxylic dianhydride.

31. The method of claim 26, wherein said at least one polymerase-inhibiting agent is an antibody against said thermostable DNA polymerase.

32. The method of claim 1, wherein the first and second primers independently have a length of at least 16 nucleotides.

33. The method of claim 1, wherein the annealing and synthesis of the thermocycling reaction are carried out at a temperature of at least about 55° C.

34. A method for sequencing at least a portion of a DNA involving simultaneously amplifying said DNA and generating truncated copies of said DNA for sequencing, comprising the steps of
(a) subjecting a mixture, in a single step, to DNA amplification and generation of truncated copies of said DNA by subjecting the mixture to a thermocycling reaction, the thermocycling reaction comprises heat denaturation, annealing and synthesis, wherein said mixture comprises said DNA,
a first primer which is able to hybridize with a strand of said DNA,
a second primer which is able to hybridize with a strand of DNA complementary to the strand with which the first primer is able to hybridize, wherein at least one of the first and second primers is labelled,
a reaction buffer,
deoxynucleotides or deoxynucleotide derivatives, wherein said deoxynucleotide derivatives are able to be incorporated by a thermostable DNA polymerase into growing DNA molecule, in place of one of dATP, dGTP, dTTP or dCTP, m
at least one dideoxynucleotide or another terminating nucleotide
a thermostable DNA polymerase having a reduced, compared to wild-type Taq DNA polymerase, discrimination against the incorporation of dideoxynucleotides relative to deoxynucleotides, and
at least one polymerase-inhibiting agent against said thermostable DNA polymerase, which polymerase-inhibiting agent loses inhibitory ability, thereby allowing said thermostable DNA polymerase to be active, at a temperature which is at least the temperature at which unspecifically hybridized primers separate from a DNA molecule, to simultaneously make full-length and truncated copies of said DNA, wherein the full-length copies have a length equal to that of at least a portion of said DNA spanning the binding sites of the first and second primers;
(b) separating at least the truncated copies of said DNA to obtain a sequence ladder; and thereafter
(c) reading the sequence ladder to obtain the sequence of said at least a portion of said DNA.

35. The method of claim 34, wherein the deoxynucleotide derivatives are thionucleotides, 7-deaza-2'-dGTP, 7-deaza-2'-dATP or deoxyinosine triphosphate.

36. The method of claim 34, wherein said another terminating nucleotide is 3'-aminonucleotide or a nucleotide having an ester group at the 3' position.

37. The method of claim 34, wherein said thermostable DNA polymerase is a Taq DNA polymerase lacking 5'-3' exonuclease activity and having a Tabor-Richardson mutation or a functional derivative thereof.

38. The method of claim 37, wherein said thermostable DNA polymerase is AMPLITAQFS, TAQUENASE, THERMOSEQUENASE, or functional derivatives thereof.

39. The method of claim 38, wherein said thermostable DNA polymerase is THERMOSEQUENASE or a functional derivative thereof.

40. The method of claim 34, wherein the thermocycling reaction in step (a) is carried out without interruption in a single container, vessel or tube.

41. The method of claim 34, wherein the initial molar ratio of said first primer to said second primer is not equal to 1:1 in step (a).

42. The method of claim 41, wherein the initial molar ratio of said first primer to said second primer is 2:1 to 3:1 in step (a).

43. The method of claim 42, wherein the initial molar ratio of said first primer to said second primer is 2:1 in step (a).

44. The method of claim 34, wherein the first and second primers are differently labelled.

45. The method of claim 34, wherein the first and second primers independently have a length of at least 25 nucleotides.

46. The method of claim 34, wherein the initial ratio of said deoxynucleotides and deoxynucleotide derivatives to said dideoxynucleotide and another terminating nucleotide in mixture A is between 100:1 and 1000:1.

47. The method of claim 46, wherein the initial ratio of said deoxynucleotides and deoxynucleotide derivatives to said dideoxynucleotide and another terminating nucleotide in mixture A is between 300:1 and 600:1.

48. The method of claim 34, wherein the initial concentrations of said deoxynucleotides or deoxynucleotide derivatives in said mixture are between 300 $\mu$M and 2 mM.

49. The method of claim 48, wherein the initial concentration of said dideoxynucleotide or another terminating nucleotide in said mixture is between 1 and 5 $\mu$M.

50. The method of claim 34, wherein said mixture further comprises at least one thermostable pyrophosphatase.

51. The method of claim 34, wherein the annealing and synthesis of the thermocycling reaction are carried out at a temperature of at least 66° C.

52. The method of claim 34, wherein the annealing and synthesis of the thermocycling reaction are carried out at a temperature of at least about 68° C.

53. The method of claim 34, wherein said DNA in said mixture is obtained from a body fluid, hairs, an individual cell, cells or fractions thereof, a tissue or fractions thereof, a cell culture or fractions thereof, a tissue culture or fractions thereof, a bacteria or a virus.

54. The method of claim 34, wherein said DNA in said mixture is a DNA in a complex mixture of nucleic acids.

55. The method of claim 54, wherein said DNA in said mixture is a DNA mixed with total genomic DNA.

56. The method of claim 55, wherein said total genomic DNA is unpurified.

57. The method of claim 34, wherein said DNA in said mixture is unpurified DNA.

58. The method of claim 34, wherein said DNA in said mixture is a DNA from single copy genes.

59. The method of claim 34, wherein said at least one polymerase-inhibiting agent is a compound containing at least one acid anhydride group per molecule.

60. The method of claim 59, wherein said at least one polymerase-inhibiting agent is citraconic anhydride, cis-aconitic anhydride, phthalic anhydride, succinic anhydride, or maleic anhydride.

61. The method of claim 60, wherein said at least one polymerase-inhibiting agent is a compound having at least two acid anhydride groups per molecule.

62. The method of claim 61, wherein said at least one polymerase-inhibiting agent is pyromellitic dianhydride or naphthalenetetracarboxylic dianhydride.

63. The method of claim 60, wherein said at least one polymerase-inhibiting agent is citraconic anhydride or cis-aconitic anhydride.

64. A kit for sequencing at least a portion of a DNA comprising deoxynucleotides or deoxynucleotide derivatives, which deoxynucleotide derivatives are able to be incorporated by a thermostable DNA polymerase into growing DNA molecules in place of one of dATP, dGTP, dTTP or dCTP;
- at least one dideoxynucleotide or another terminating nucleotide;
- a thermostable DNA polymerase having a reduced, compared with wild-type Taq polymerase, discrimination against the incorporation of dideoxynucleotides relative to deoxynucleotides, and
- at least one polymerase-inhibiting agent against said thermostable DNA polymerase, which polymerase-inhibiting agent loses inhibitory ability, thereby allowing said thermostable DNA polymerase to be active, at a temperature which is at least the temperature at which unspecifically hydridized primers separate from a DNA molecule.

65. The kit of claim 64, wherein said deoxynucleotide derivatives are thionucleotides, 7-deaza-2'-dGTP, 7-deaza-2'-dATP or deoxyinosine triphosphate.

66. The kit of claim 64, wherein said another terminating nucleotide is a 3'-aminonucleotide or a nucleotide having an ester group at the 3'position.

67. The kit of claim 64, wherein said thermostable DNA polymerase is a Taq DNA polymerase lacking 5'-3'exonuclease activity and having a Tabor-Richardson mutation or a functional derivative of the Tabor-Richardson mutation.

68. The kit of claim 64, wherein said thermostable DNA polymerase is AMPLITAQFS, TAQUENASE, THERMOSEQUENASE, or functional derivatives thereof.

69. The kit of claim 68, wherein said thermostable DNA polymerase is THERMOSEQUENASE, or a functional derivative thereof.

70. The kit of claim 64, further comprising at least one thermostable pyrophosphatase.

71. The kit of claim 64, wherein the molar ratio of said deoxynucleotides and deoxynucleotide derivatives to said dideoxynucleotide and another terminating nucleotide is between 100:1 and 1000:1.

72. The kit of claim 71, wherein the molar ratio of said deoxynucleotides and deoxynucleotide derivatives to said dideoxynucleotide and another terminating nucleotide is between 300:1 and 600:1.

73. The kit of claim 64, wherein said at least one polymerase-inhibiting agent is a compound containing at least one acid anhydride group per molecule.

74. The kit of claim 73, wherein said at least one polymerase-inhibiting agent is citraconic anhydride, cis-aconitic anhydride, butyric anhydride, acetic propionic anhydride, phthalic anhydride, succinic anhydride, maleic anhydride or phthalic anhydride.

75. The kit of claim 64, wherein said at least one polymerase-inhibiting agent is a compound having at least two acid anhydride groups per molecule.

76. The kit of claim 75, wherein said at least one polymerase-inhibiting agent is pyromellitic dianhydride or naphthalenetetracarboxylic dianhydride.

77. The kit of claim 74, wherein said at least one polymerase-inhibiting agent is citraconic anhydride or cis-aconitic anhydride.

78. The kit of claim 64, further comprising first and second primers, wherein
(1) said first primer is able to hybridize with a strand of a DNA to be sequenced, and
(2) said second primer is able to hybridize with a strand of a DNA complementary to the strand with which said first primer is able to hydridize, wherein at least one of the first and second primers is labelled.

79. The kit of claim 78, wherein the molar ratio of said first primer to said second primer is different from 1:1.

80. The kit of claim 79, wherein the molar ratio of said first primer to said second primer is 2:1 to 3:1.

81. The kit of claim 80, wherein the molar ratio of said first primer to said second primer is 2:1.

82. The kit of claim 78, wherein the first and second primers are differently labelled.

83. The kit of claim 78, wherein the first and second primers independently have a length of at least 16 nucleotides.

84. The kit of claim 83, wherein the first and second primers independently have a length of at least 25 nucleotides.

85. The method of claim 34, wherein the first and second primers independently have a length of at least 16 nucleotides.

86. The method of claim 34, wherein the annealing and synthesis of the thermocycling reaction are carried out at a temperature of at least about 55° C.

87. The method of claim 1, wherein said thermostable DNA polymerase is Tth DNA polymerase having a Tabor Richardson mutation.

* * * * *